United States Patent

Wan

[11] Patent Number: 5,855,599
[45] Date of Patent: Jan. 5, 1999

[54] SILICON MICRO MACHINED OCCLUSION IMPLANT

[75] Inventor: Lawrence A. Wan, Malibu, Calif.

[73] Assignee: Sitek, Inc., Sylmar, Calif.

[21] Appl. No.: 921,775

[22] Filed: Sep. 2, 1997

[51] Int. Cl.[6] .................................................... A61F 2/06
[52] U.S. Cl. .............................. 623/1; 606/193; 606/194; 606/200; 128/831; 128/830
[58] Field of Search .................................. 128/830, 833, 128/831, 843; 606/194, 198, 200, 157, 193; 623/1, 11, 12

[56] References Cited

U.S. PATENT DOCUMENTS

| | | | |
|---|---|---|---|
| 3,540,431 | 11/1970 | Mobin-Uddin | 128/831 |
| 3,810,456 | 5/1974 | Karman | 128/831 |
| 4,135,495 | 1/1979 | Borgen | 128/831 |
| 4,446,579 | 5/1984 | Inamori et al. | 623/18 |
| 4,623,355 | 11/1986 | Sawruk | 623/66 |
| 5,413,586 | 5/1995 | Dibie et al. | 606/200 |
| 5,601,600 | 2/1997 | Ton . | |
| 5,693,067 | 12/1997 | Purdy | 606/200 |

*Primary Examiner*—Michael J. Milano
*Assistant Examiner*—Tram A. Nguyen
*Attorney, Agent, or Firm*—Flehr Hohbach Test Albritton & Herbert LLP

[57] ABSTRACT

An occlusion implant device for small body lumens consisting of a micromachined monocrystalline silicon disk which has inherently spring loaded integral helical wings which when released by the insertion device anchors the implant in position. The device may be used for contraception vaso-occlusion for treatment of aneurysms and with an aperture therethrough may also be utilized as a stent. Alternatively, a micro mold of silicon may be formed and a metal or plastic disk produced by injection molding.

11 Claims, 5 Drawing Sheets

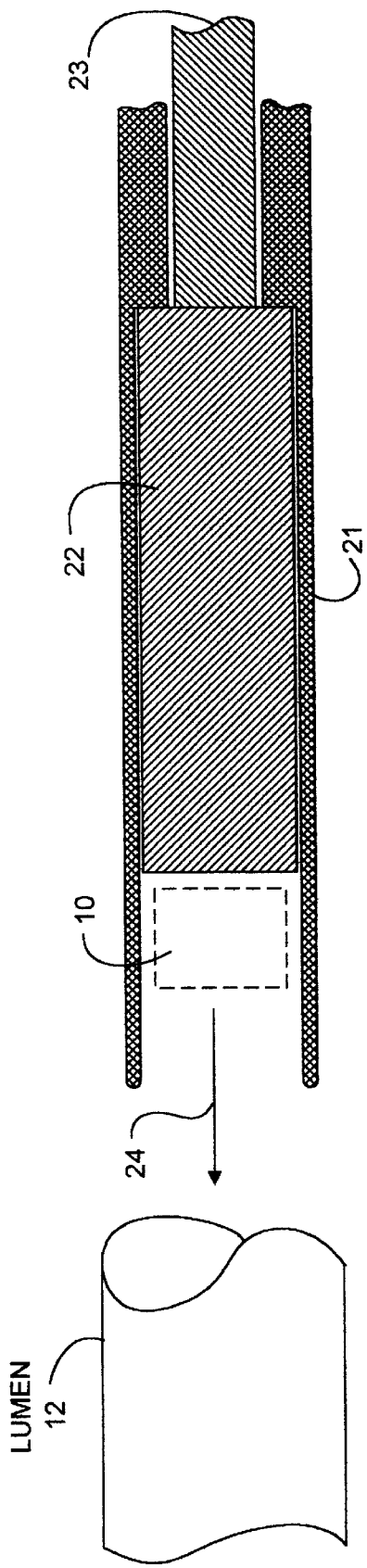
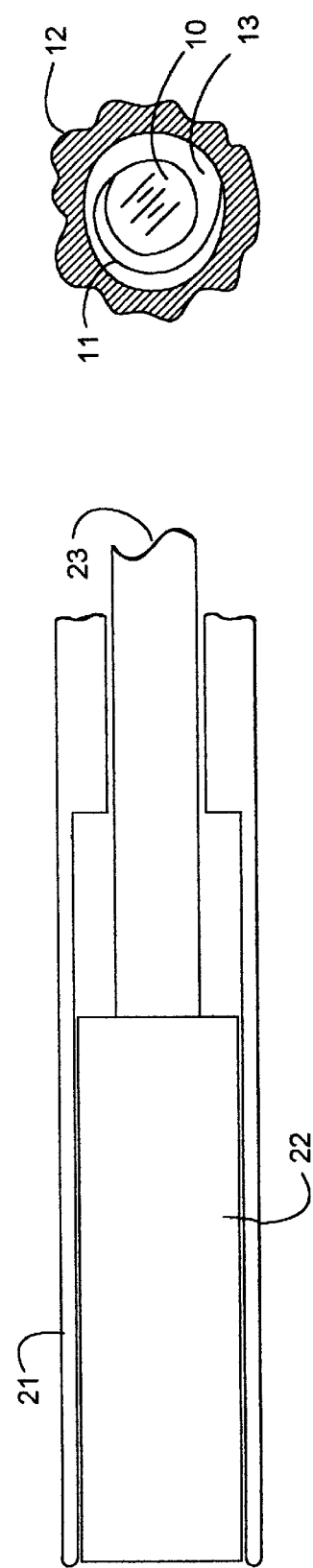
FIG. 5
FIG. 6
FIG. 7

SILICON MICRO MACHINED OCCLUSION IMPLANT

The present invention is directed to a silicon micro machined occlusion implant, and more particularly to an implant suitable for use in very small body lumens.

BACKGROUND OF THE INVENTION

Endoscopic techniques for human medical use are becoming much more prevalent.

For example, as disclosed in U.S. Pat. No. 5,601,600, endoluminal coils have been used both in the treatment of vascular aneurysms to occlude the site to thus act as a barrier to blood flow and also as an intrafallopian coil for contraceptive use. Such coils are generally composed of a wound resilient alloy wire having a dimension which is in the low millimeter range. This is much too large for the interior of the fallopian tube or other blood vessels which are significantly smaller. Thus there is a need for an occlusive implant device which is suitable for very small body lumen.

OBJECT AND SUMMARY OF THE INVENTION

It is therefore an object of the present invention to provide an improved occlusion implant for a very small body lumen as well as a process of installing such implant.

In accordance with the above object there is provided an occlusion implant for a very small body lumen comprising a unitary monocrystalline semiconductive disk having at least one integral spring loaded helical wing for frictionally contacting the wall of the lumen to maintain the disk in position. At the same time it also provides a small enough opening to prevent passage of unwanted fluid material downstream in said lumen. A process of installing the occlusion implant is also provided along with the use of an occlusion implant with a central opening to serve as a stent.

BRIEF DESCRIPTION OF THE DRAWINGS

FIG. 5 shows a catheter technique of installing an occlusion implant of the present invention.

FIG. 6 is a side view of a portion of FIG. 5 in a different condition.

FIG. 7 is a cross section of a body lumen with an occlusion implant.

DETAILED DESCRIPTION OF PREFERRED EMBODIMENTS

Figure 1:
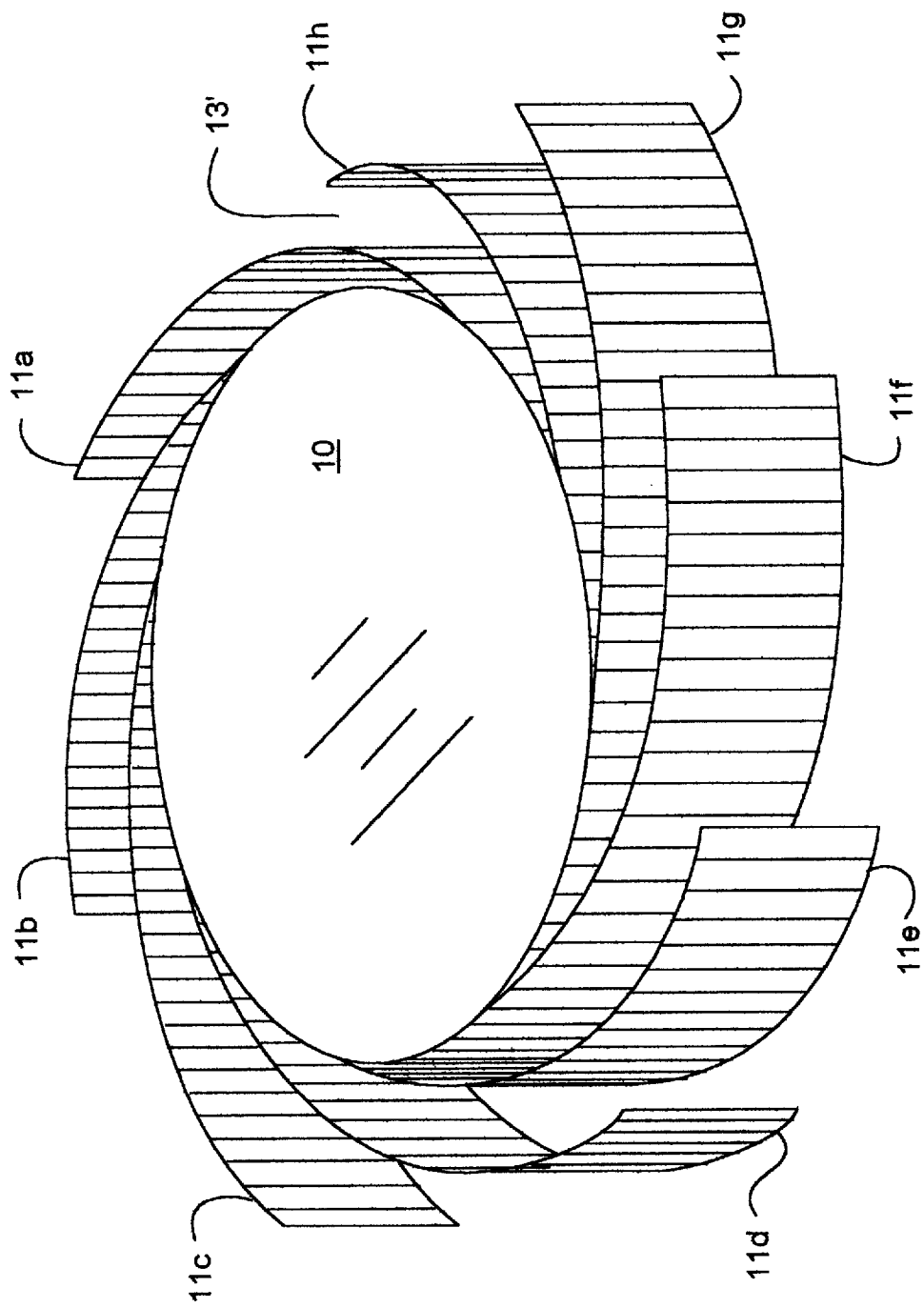
FIG. 1 is a perspective view of an occlusion implant embodying the present invention.

FIG. 1 illustrates the occlusion implant of the present invention which includes a central unitary monocrystalline silicon disk 10 having a plurality of integral helical wings 11a–11h, These extend in a spiral manner from the disk wrapping around the cylinder which constitutes the disk. In other words they form a spiral. The semiconductive material of which the disk is made of is preferably biocompatible so as not to be rejected by the human body and it is believed silicon is an ideal material.

Moreover, to provide the spring loading effect of the helical wings 11a–11h it is necessary to use a monocrystalline structure rather than a polycrystalline structure.

When the structure of FIG. 1 is constructed by well known silicon micromachining techniques, the wings 11a–11h are inherently spring loaded. In other words they are resilient. When the disk is inserted in a body lumen, either for example a fallopian tube or a blood vessel or other body passageway, expansion of the wings (or at least one wing) will cause a frictional contact with the wall of the lumen to maintain disk 10 in position. In addition at the same time when the wings are compressed by the body lumen 12 (see briefly FIG. 7) the open interstices left in the helix are small enough, for example, as illustrated at 13 and 13' (see FIG. 1) to occlude or prevent the passage of particles or fluid.

The implant device of FIG. 1 is silicon micro machined in accordance with well known techniques which include the steps of masking and etching. Such micro machining technique is discussed in a publication, a final report of the Department of Defense dated December 1995 entitled "Microelectromechanical Systems". This is abbreviated "MEMS". With such a technique heretofore unobtainable miniature dimensions are possible. When the disk of FIG. 1 is used, for example, for contraceptive use in a fallopian tube, it would have a diameter of approximately 500 to 1000 microns and a similar depth. And any resulting opening 13 would be 50 microns more or less to thus provide an effective block to fluid or particles downstream of the occlusion implant. Even smaller dimensions are obtainable where the device can be used for vaso-occlusions for the treatment of aneurysms. One region of the body where, of course, the blood vessels are very small would be in the brain. Thus the silicon disk may be manufactured from an off the shelf silicon normally used for integrated circuits. Where the implant of FIG. 1 (or the other alternative implants to be discussed below) is used as a contraceptive device, it may be X-ray opaque by copper plating; this will also induce fibrosis which is desired. It may also be impregnated with tetracyclins for inducing inflammation and fibrosis.

Figure 4:
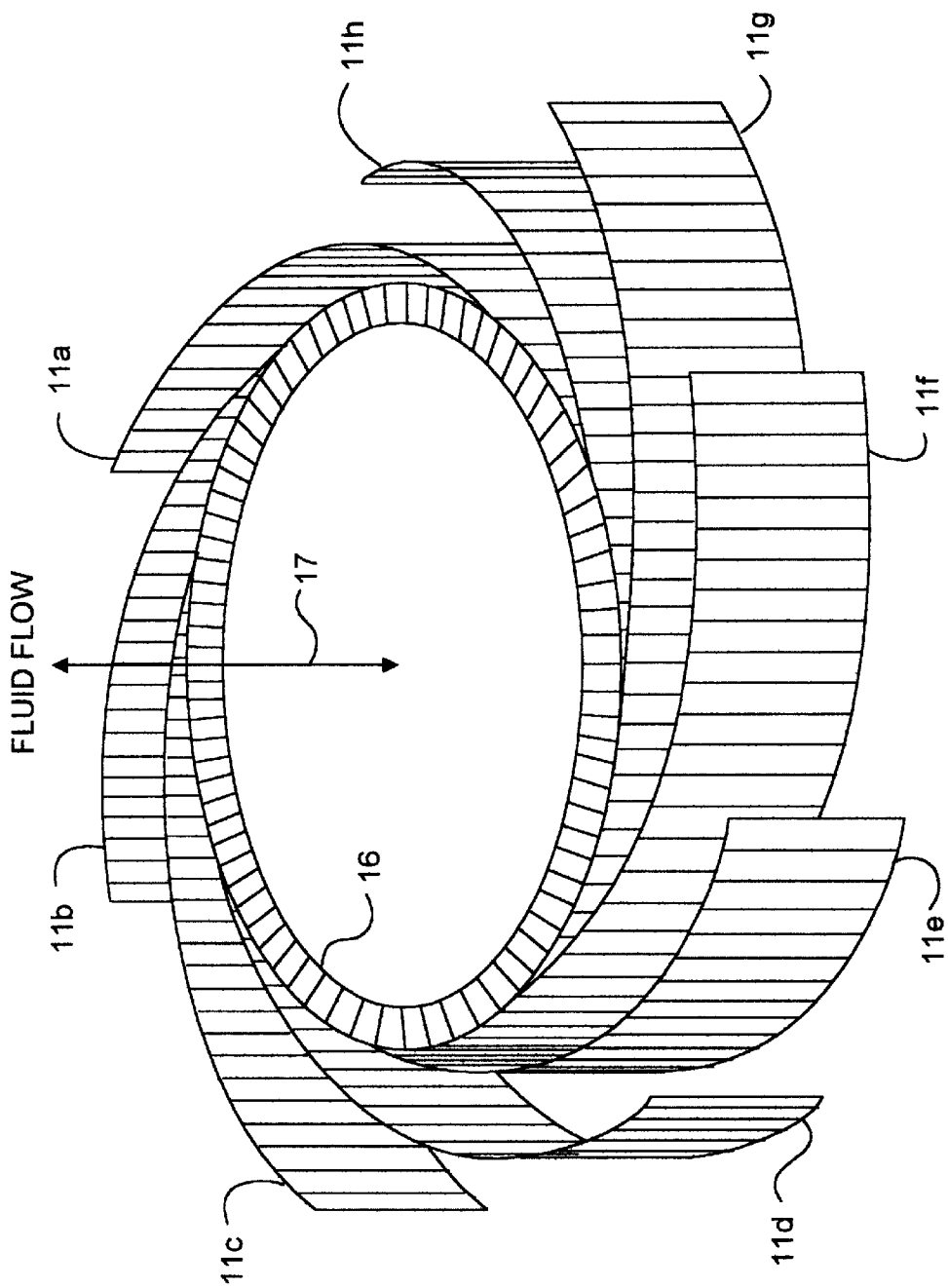
FIG. 4 is a perspective view of an alternative embodiment of FIG. 1.

FIG. 4 illustrates an alternative construction for use as a stent where the disk 10 includes the machined wings 11a–11h but also has a central aperture 16 which allows fluid flow through it indicated by the arrow 17. The spring action of the wings 11a–11h when released in, for example, the blood vessel, press against the vessel to enlarge or open the vessel thus acting as a stent. Such stents because of the novel concept of the present invention in using silicon micro machining, may be used in very small blood vessels or lumens. In fact, in the present invention, the term lumen which includes body passageways such as a fallopian tube, will also include blood vessels.

Figure 2:
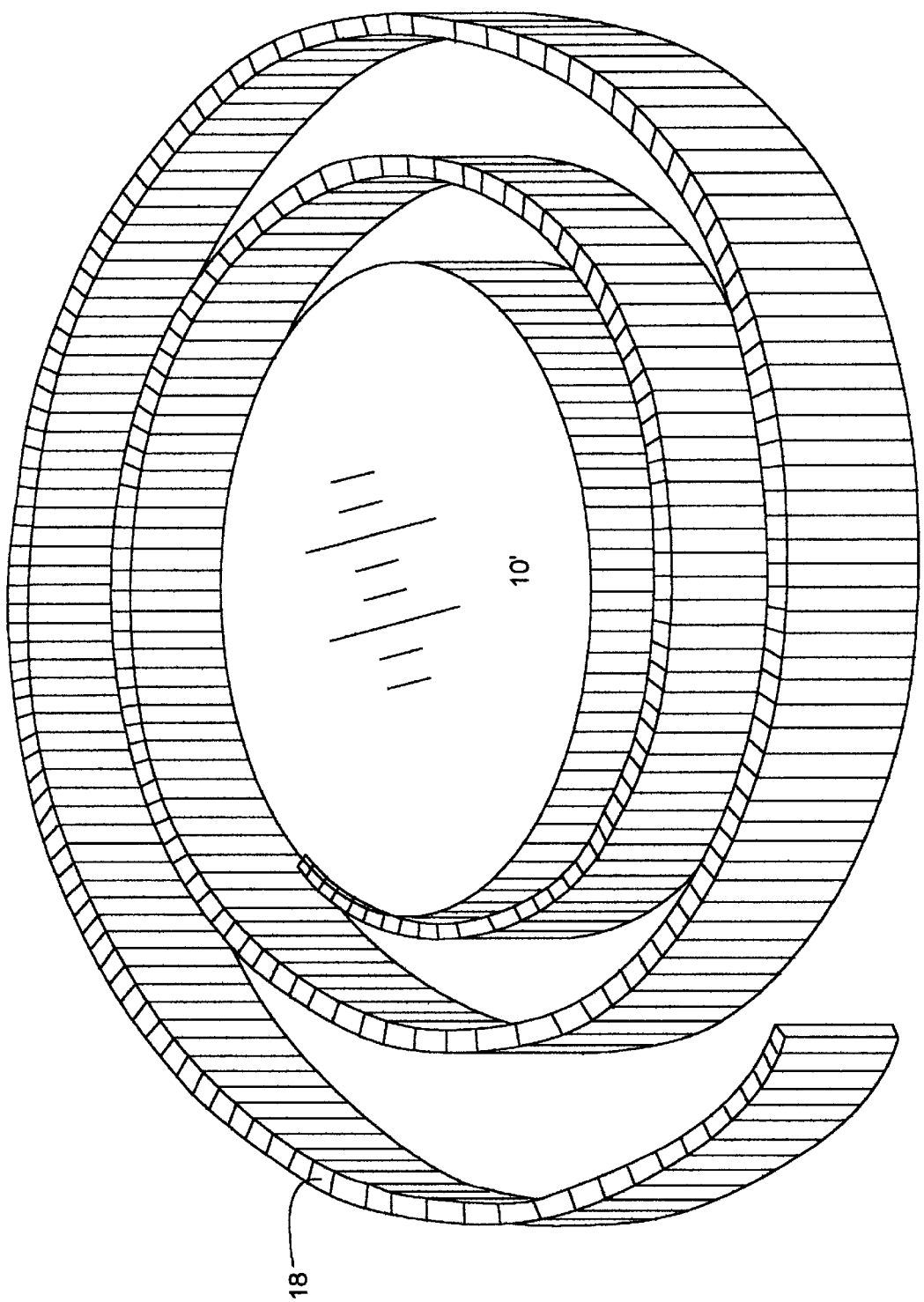
FIG. 2 is a perspective view of an alternative embodiment of FIG. 1.

FIG. 2 is an alternative embodiment of the occlusive device of FIG. 1 but instead of the multiple helical wings 11a–11h has only a single spiral or helical wing 18 which is wrapped around the disk 10'.

Figure 3:
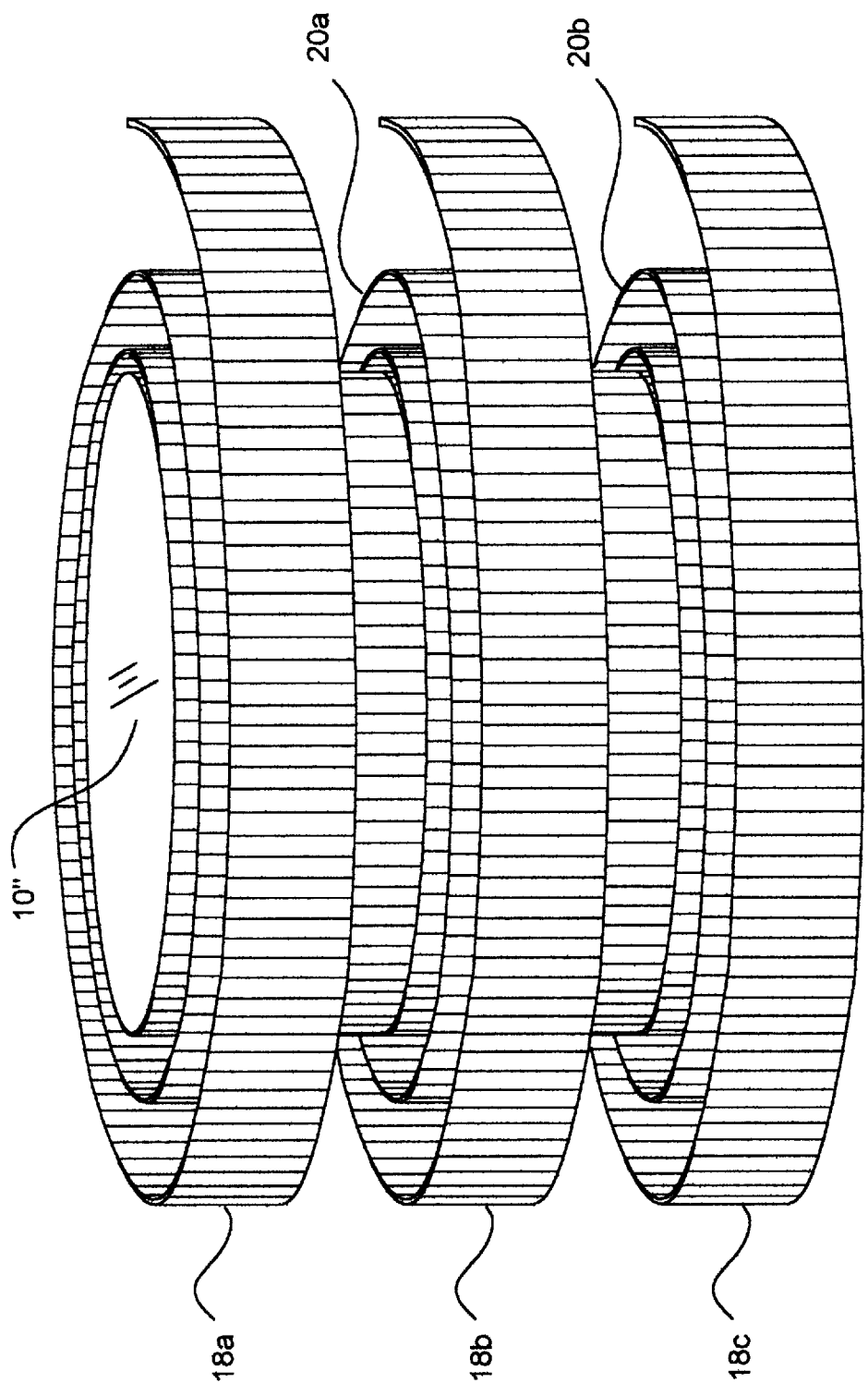
FIG. 3 is a perspective view of an alternative embodiment of FIG. 1.

Finally FIG. 3 is another embodiment where a disk 10" has wrapped around it a coil such as 18 but as a set of 3, 18a, 18b, 18c, which are vertically stacked with intermediate spacer disks 20a and 20b. This entire vertical assembly is unified by silicon wafer fusion bonding. And, of course, a similar stack construction may be 10 used for the stent device of FIG. 4.

To deliver or install the occlusion implant device 10 in a body lumen 12, a catheter in the form of a slidable collar 21 (see FIG. 5) normally retains the implant device 10 against the inner catheter cylinder 22 which has a tail 23 extending from its end use for insertion of the catheter in the body lumen 12. As shown by the arrow 24 the implant, by use of the catheter, is inserted in the body lumen 12 to the desired position or location. Before insertion, of course, the slidable collar 21 retains the wings 11 of the disk 10 in retracted position,. However, after insertion, retraction of the sleeve 21 as shown in FIG. 6 releases the disk 10 in the lumen 12 and the wing 11, or the plurality of wings, expands to contact the wall of the lumen to retain the disk in position. Furthermore, as discussed above, the space 13 which is greatly enlarged in FIG. 7, is small enough to restrict the passage of any significant particles or fluid.

The same insertion technique may be used for the stent device (see FIG. 4) where of course, blood would be allowed to flow through with the stent merely stretching or keeping open the vessel.

Although the use of monocrystalline silicon is believed to be optimal for the occlusion implants of the present invention, it is also possible to form the implants from either plastic or metal. This could be done by the process of, for example, etching a silicon die or disk to form a micro mold having the proper dimension for the desired implant device including the helical wings. And then by either casting or injection molding, the implant device is produced. Titanium or stainless steel are ideal metals. With the proper dimensions these would have helical wings which are effectively spring loaded. And for use in the body, of course, these metals are already approved by the United States Food and Drug Administration. If high aspect ratios are desired then a deep plasma etch can be used to achieve precise dimensionality in a molding cavity. And even plastic micro miniature devices can be produced by the foregoing technique.

Thus in summary the miniaturization of an occlusion device by micromachining and the fact that monocrystalline semiconductor material such as silicon has a natural spring effect provides an ideal occlusion or stent device. Because of the small size the implant may be inserted in locations hereto otherwise not reachable. This is especially true of blood vessels in the brain. For contraceptive use the efficacy of the device is superior to other devices such as the IUD and of course is a much less intrusive alternative to tubal ligation.

Thus an improved occlusion implant and stent has been provided and also a technique for insertion.

What is claimed is:

1. An occlusion implant for a very small body lumen comprising a unitary monocrystalline semiconductive disk having at least one integral spring loaded helical wing for frictionally contacting the wall of said lumen to maintain said disk in position and at the same time to also provide a small enough opening to prevent passage of unwanted fluid material downstream in said lumen.

2. An implant as in claim 1 where said disk is produced by micromachining semiconductor techniques.

3. An implant as in claim 1 where said disk consists of a bio-compatible material.

4. An implant as in claim 3 where said material is silicon.

5. An implant as in claim 4 where said disk is vertically stacked with similar disks with at least one intermediate silicon disk and forming a unified assembly by silicon wafer fusion bonding.

6. A catheter for insertion of a occlusion implant for a very small body lumen the implant having a unitary monocrystalline semiconductive disk having at least one integral spring loaded helical wing for frictionally contacting the wall of said lumen to maintain said disk in position and at the same time to also provide a small enough opening to prevent passage of unwanted fluid material downstream in said lumen, said catheter including a slidable collar on a distal end of said catheter for retaining said spring loaded helical wing of said disk, and means for sliding said collar toward a proximal end of said catheter to release said disk and allow said helical wing to expand against said wall of said lumen to contact said wall and to thereby maintain said disk in position.

7. A process of installing an occlusion implant in a very small body lumen in the form of a unitary monocrystalline semiconductive disk having at least one integral spring loaded helical wing for frictionally contacting the wall of the lumen to maintain said disk in position comprising the following steps:
 a) providing a catheter having a slidable collar on a distal end;
 b) placing in said slidable collar said disk to thereby retain the spring wing of said disk;
 c) inserting said catheter in said lumen to a desired location;
 d) releasing said disk and said at least one helical wing of said disk for frictionally contacting the wall of said lumen by pulling back said collar toward a proximal end of said catheter.

8. A stent for a blood vessel comprising a unitary monocrystalline silicon disk having at least one integral spring loaded helical wing for frictionally contacting the wall of said blood vessel to maintain said disk in position, said disk having a central opening to allow for circulation of blood.

9. An occlusion implant for a very small body lumen comprising a unitary disk having at least one integral spring loaded helical wing for frictionally contacting the wall of said lumen to maintain said disk in position said at least one helical wing being compressed to form open interstices with said wing and said disk and said wall of said lumen said interstices providing a small enough opening to prevent passage of unwanted particle or fluid material downstream in said lumen, said entire at least one helical wing substantially lying in a common plane with said disk.

10. An implant as in claim 9 where said disk consists of metal or plastic.

11. An implant as in claim 10 where said disk is produced by the following process:
 a) etch a semiconductive material to form a micro mold,
 b) using the mold, cast or injection mold, said implant using metal or plastic.

* * * * *